(12) United States Patent
Milosevic et al.

(10) Patent No.: US 8,218,139 B2
(45) Date of Patent: Jul. 10, 2012

(54) OPTICAL MULTIPASS CELL FOR REPEATED PASSING OF LIGHT THROUGH THE SAME POINT

(76) Inventors: Milan Milosevic, Westport, CT (US); Violet Milosevic, Westport, CT (US)

( * ) Notice: Subject to any disclaimer, the term of this patent is extended or adjusted under 35 U.S.C. 154(b) by 149 days.

(21) Appl. No.: 12/767,172

(22) Filed: Apr. 26, 2010

(65) Prior Publication Data
US 2010/0201977 A1    Aug. 12, 2010

Related U.S. Application Data

(63) Continuation-in-part of application No. 12/074,137, filed on Feb. 29, 2008, now abandoned.

(60) Provisional application No. 60/904,225, filed on Mar. 1, 2007, provisional application No. 61/003,230, filed on Nov. 15, 2007.

(51) Int. Cl.
*G01J 3/44*    (2006.01)

(52) U.S. Cl. ........................................ 356/301

(58) Field of Classification Search .............. 356/72–73, 356/301, 445
See application file for complete search history.

(56) References Cited

U.S. PATENT DOCUMENTS

| | | | |
|---|---|---|---|
| 5,292,483 A * | 3/1994 | Kaye | 422/82 |
| 5,546,222 A * | 8/1996 | Plaessmann et al. | 359/346 |
| 6,577,398 B1 * | 6/2003 | Ducellier | 356/519 |

* cited by examiner

*Primary Examiner* — Tarifur Chowdhury
*Assistant Examiner* — Abdullahi Nur

(57) ABSTRACT

The present invention is a multipass unipoint optical cell used for the improved analysis of samples by transmission, reflection, Raman or fluorescence spectroscopy by the multiple reimaging of light through the same analysis point. The cell comprises two or more identical optical reimaging elements each consisting of two symmetrically opposing, identical, confocal, and coaxial parabolic reflective surfaces. These reimaging optical elements can be arranged around the common focal point, which thus becomes the analysis point, to form different multipass unipoint optical cell configurations, all the passes crossing in the analysis point where a sample is brought to interact with light, the effect of said interaction being enhanced in proportion to the number of passes.

14 Claims, 7 Drawing Sheets

OPTICAL MULTIPASS CELL FOR REPEATED PASSING OF LIGHT THROUGH THE SAME POINT

CROSS-REFERENCE TO RELATED APPLICATIONS

This application is a continuation-in-part application of patent application U.S. Ser. No. 12/074,137 by Milan Milosevic, filed Feb. 29, 2008 now abandoned, the contents of which are fully incorporated by reference herein, and which continuation-in-part application claims the benefit of provisional patent application U.S. Ser. No. 60/904,225, by Milan Milosevic, filed Mar. 1, 2007 and the benefit of provisional patent application U.S. Ser. No. 61/003,230, filed Nov. 15, 2007, by Milan Milosevic, both provisional applications are fully incorporated by reference herein.

TECHNICAL FIELD

The field of the present invention relates to optical spectroscopy. Specifically, firstly it relates to the analysis of samples by Raman, transmission, reflection or fluorescence spectroscopy. Secondly, it relates to an optical multipass unipoint cell for the enhancement of said analysis by repeatedly reimaging the light back into the same analysis point. Thirdly, it relates to the special configuration of the reimaging system whereby the reflectance losses are recycled back for analysis thus improving the efficacy of the gain achieved by the multipass configuration.

BACKGROUND

In analyzing samples in spectroscopy, light is passed through an analysis point in which it interacts with the sample placed at that point causing either the absorption of said light or the emission of a secondary light (such as Raman, fluorescence, etc.) by the sample. Both, the degree to which the light is absorbed, and the intensity and spectral characteristics of the emitted secondary light are influenced by the nature of the sample present in the analysis point. In this way a sample can be identified, the composition of a mixture quantified, etc. In some cases the absorption of light or the secondary emitted light are too weak to be reliably measured. One way this was traditionally addressed was by passing light multiple times through the sample using so called multipass cells.

It is common in so called attenuated total reflection (ATR) spectroscopy [N. J. Harrick: Internal Reflection Spectroscopy, Harrick Scientific Corporation, Ossining N.Y., 1987.] to employ a multipass cell comprising an optical element that has two parallel surfaces through which light propagates by reflecting in a zigzag fashion between said surfaces. If an absorbing sample is pressed against one or both of the flat surfaces, the attenuation of light that occurs at a single reflection is magnified by the multiple reflections. Although the effect is thus magnified, in each of these multiple reflections light interacts with a different portion of the sample requiring a large quantity of the sample for analysis. This can be a problem in those cases where only a small amount of sample is available.

Another example of a multipass cell is the so called White cell [John U. White, "Long Optical Paths of Large Aperture", J. Opt. Soc. Am, No. 32 (1942), pp 285-288] routinely used for the analysis of gases by transmission spectroscopy. Light enters the cell and is reflected between a special arrangement of three spherical mirrors a large number of times until it exits the cell. The absorption of light by the gas in the cell is enhanced by the extended path provided by the cell's optics. These cells work well for absorption spectroscopy, but cannot be used to study gasses by Raman or fluorescence spectroscopy. Each pass through the White cell is distinct from all the other passes and there is no crossing point that could be the source of secondary emissions enhanced by multiple passes of light through said crossing point.

In order to use multipass cells for Raman, fluorescence, etc. studies of gasses a unipoint multipass cell was introduced [R. A. Hill, A. J. Mulac and C. E. Hackett, Retroreflecting Multipass Cell for Raman Scattering, Appl. Opt. 16 (1977) 2004-2008] that provided that all the passes cross in a single point. This crossing point of light is also the analysis point of the cell. A sample placed in this point interacts with all the passes through the cell greatly enhancing secondary emissions from this point. The unipoint multipass operation was achieved by two sets of retro-reflectors accompanied by two lenses. The midpoint between the lenses was also a focal point for the two lenses. Collimated light was retro-reflected back to the cell by the retro reflectors and refocused into the focal point by the lenses. By slightly offsetting one of the retro reflectors, the returning light is slightly offset with respect to the incoming light thus enabling multiple passes. After a number of passes, light falls out of the aperture of one of the lenses and exits the cell. The light intensity of every returning pass is reduced by reflection losses in the retro reflectors and on the lenses. Thus, after a number of passes, the intensity of the returning light is weakened sufficiently to offset the benefit of multiple passes.

Ducellier (U.S. Pat. No. 6,577,398B1) utilized the essential part of the Hill concept of a retro reflector and a lens to set up a resonant optical cavity. Only one set of a retro reflector and a lens arrangement of Hill was used and the multipass configuration was achieved by placing a beamsplitter into the focal point of the lens. The beamsplitter provided a partial return of the exiting light back into the cell therefore replacing the second set of a retro reflector and a lens from Hill.

Both Hill and Ducellier devices used a lens in combination with a retro reflector. All lenses suffer from spherical and chromatic aberrations. The spherical aberration of a lens is responsible for blurring of the image. All rays in a collimated beam entering a lens are not brought into a sharp point in the focus of the lens, but are spread over a small area around the focus. Lenses can be designed in a way that minimizes the size of the blur, but never to completely eliminate it. Repeated passes further degrade the imaging thereby limiting the number of passes that can be employed in the cell. Chromatic aberration of a lens is a consequence of the fact that the focal point of a lens is a function of the refractive index of the material that the lens is made of. Since the refractive index of materials changes with wavelength, the focal point of a lens is slightly different for different wavelengths of light. This means that for a beam containing multiple wavelengths of light, the cell can never be brought in alignment for all wavelengths simultaneously. Although techniques exist to minimize these aberrations, they bring in a high level of complexity and expense. The minimization of the aberrations can only be achieved over a relatively narrow range of wavelengths so a different cell has to be used for each range of wavelengths of light. In addition to the aberrations, reflection losses that light encounters in passing through the devices of Hill and Ducellier include four reflection losses on the lens and two reflection losses on the two mirrors of the retro reflector for each pass through the device. Again, techniques exist to minimize these loses, but they are effective only over a narrow range of wavelengths and add considerable complexity and expense.

A variation of the multipass cell configuration was introduced [J. C. Robinson, M. Fink and A. Mihill, New Vapor Phase Spontaneous Raman Spectrometer, Rev. Sci. Instrum. 63 (1992), 3280-3284] that utilizes two crossing points so that all the passes cross in one or the other point. Each of the points can become the source of Raman, fluorescence, etc. emissions. This cell design was an improvement on the unipoint multipass cell [Hill et al.] since it used only two spherical mirrors and thus had reduced reflectance losses. While the reflectance losses are reduced, they still limit the number of passes that can be effectively utilized by the cell. Also, having two crossing points instead of one reduces the gain achieved due to multiple passes.

Another version of the unipoint multiple pass concept has been proposed by Harrick [N. J. Harrick: Internal Reflection Spectroscopy, Harrick Scientific Corporation, Ossining N.Y., 1987.] for the ATR analysis of samples. This concept, however, was never reduced to practice because the shape of the ATR crystal required for the operation was too complex to manufacture and the optical design was not suitable for the reimaging of a typical spectrometer beam. However, it was recognized that if such a unipoint multipass cell could be developed, that it would be of great utility in ATR spectroscopy.

Thus there is a need for a system that can overcome the above and other disadvantages.

SUMMARY OF THE INVENTION

The current invention relates to an optical reimaging element comprising: a first off-axis parabolic mirror having only the portion of the mirror surface below the first plane that passes through its focal point and is perpendicular to the axis of the first parabola associated with the first mirror, the portion of the first mirror being on the same side of the first plane as the vertex of the first parabola; a second off axis parabolic mirror identical to the first mirror also having only the portion of the mirror surface below the second plane that passes through its focal point and is perpendicular to the axis of the second parabola associated with the second mirror, the portion of the second mirror being on the same side of the second plane as the vertex of the second parabola; and the first and second mirrors being in optical communication with each other so that their first and second planes coincide and so that their parabolic mirror surfaces are symmetrically opposing, confocal, and coaxial thereby having the property that a ray of light coming from the common focal point of the parabolic mirrors and incident onto one of the parabolic mirrors reflects to the other parabolic mirror wherein it reflects back to the focal point, but at an angle with the direction in which it left the focal point.

The current invention also relates to an optical reimaging element made from: an optically transparent material comprising: a top face; a bottom face; a first side face; a second side face; a third side face; and where the first and second of the side faces are in the shape of two symmetrically opposing, confocal, and coaxial parabolic surfaces so that the common axis of the parabolic surfaces is parallel and midway between the top and bottom faces and the third side face is spherical with the center of curvature coincident with the common focal point of the parabolic surfaces so that any ray of light originating from the common focal point and directed to the element is incident normal to the third face, transmits into the element without changing direction, is incident on one of the parabolic surfaces, reflects by total internal reflection to the other of the two parabolic surfaces, is reflected again by total internal reflection to come at normal incidence to the third face, transmits out of the element without changing direction and returns to the common focal point at an angle to the direction in which it left the focal point.

BRIEF DESCRIPTION OF THE DRAWINGS

The present disclosure will be better understood by those skilled in the pertinent art by referencing the accompanying drawings, where like elements are numbered alike in the figures, in which.

DETAILED DESCRIPTION

Figure 1:
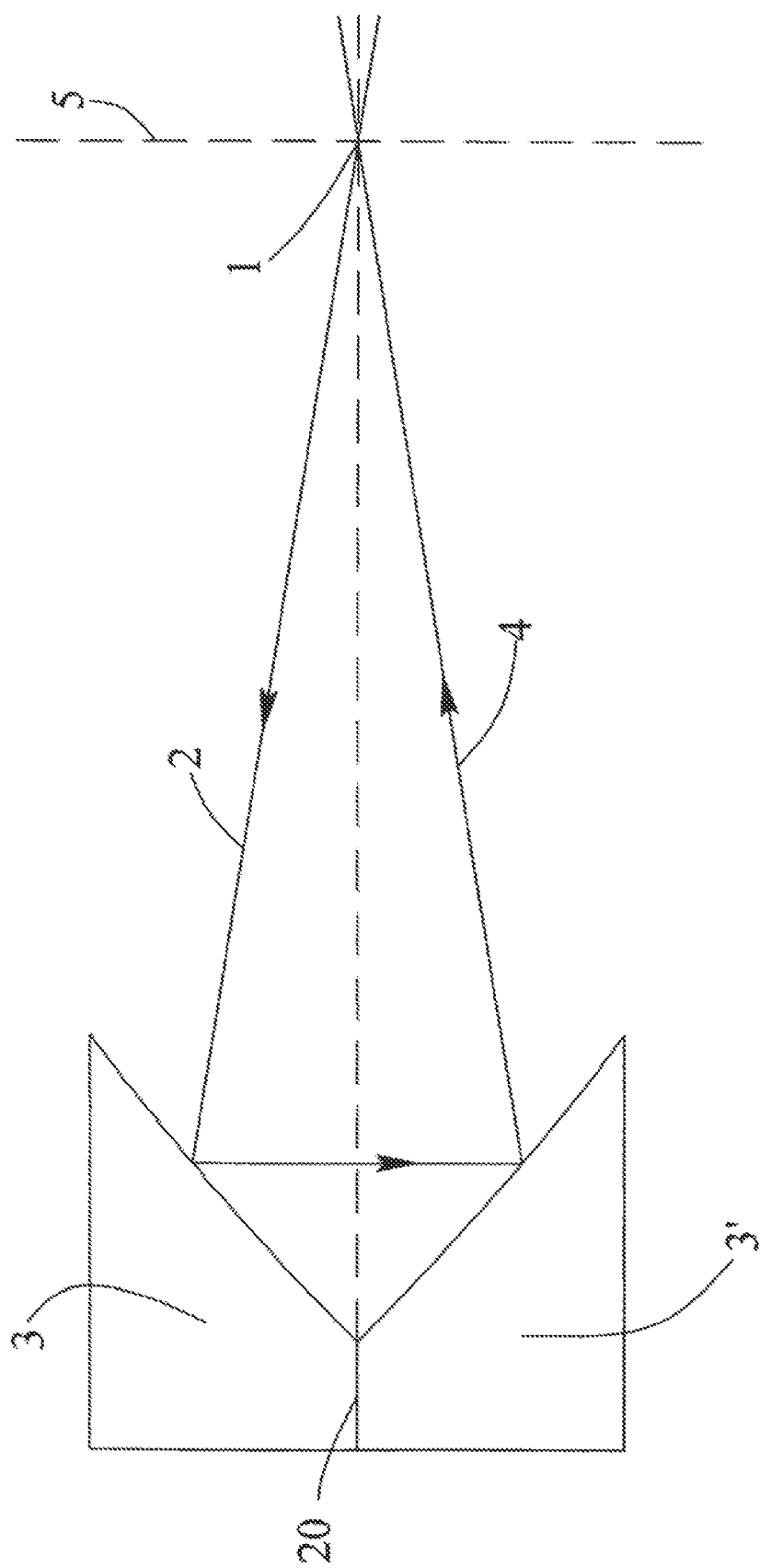
FIG. 1 discloses a unipoint multipass concept based on an optical reimaging element (ORIE) consisting of two opposing confocal coaxial parabolic reflective surfaces 3 and 3', wherein focal point 1 is common to both parabolic surfaces, a ray 2 coming from the focal point anywhere onto reflecting surface 3 is reflected to surface 3' and refocused as ray 4 back to the focal point 1.

Reference Numerals for the patent figures:
1 Focal point of a reimaging element

2 Incoming ray
3 First parabolic mirror
3' Second parabolic mirror
4 Outgoing ray
5 Axis of the two parabolic surfaces
6 First ORIE
7 Second ORIE
8 Focal point of two ORIEs multipass configuration
9 Outgoing ray
10 Incoming ray
11 First reflective parabolic surface
12 Second reflective parabolic surface
13 Spherical entrance/exit surface
14 Focal point of solid ORIE
15. Hemispherical ATR element
16 ORIEs
17 Center of hemispherical ATR element
18 Outgoing secondary emitted radiation
20 Cutting plane for parabolic mirrors The optical multipass unipoint cell configurations described herein are based on the special optical property of the ORIE consisting of two symmetrically opposing, identical, confocal, and coaxial parabolic reflective surfaces to reimage any ray of light coming from the common focal point onto one of said parabolic surfaces, back to said focal point by the other parabolic surface.

One way in which this ORIE can be made is by assembling together a pair of identical parabolic mirrors 3 and 3' as shown in FIG. 1. An off axis parabolic mirror is made by one of the standard techniques such as diamond turning. The flat surface 20 is then cut into the mirror through the focal point 1 and perpendicular to the axis of the parabola 5. Two such identical mirrors 3 and 3' are turned face to face in a mirror image fashion and joined together on said cut surfaces 20. The two parabolic surfaces thus arranged have a common axis 5 and a common focal point 1 and are mutually symmetrical with respect to surface 20. Alternatively, the entire ORIE could be molded as one piece. This particular arrangement of two parabolic reflecting surfaces has the property that any light ray 2 coming from the common focal point 1 anywhere onto the entrance mirror 3 is reflected parallel to the common axis toward exit surface 3' and then reflected back into the focal point 1 by the surface 3'. The returned ray 4 is at an angle with the incoming ray 2.

Prior art [Hill, Ducellier] aimed at achieving this optical functionality by employing a lens and a retro reflector. The result was a device that achieved the desired functionality only approximately. It suffered from spherical and chromatic aberrations due to the lens and also from reflection losses occurring on the lens and the mirrors. The configuration of two coaxial, confocal symmetrically opposing reflective parabolic surfaces shown in FIG. 1 represents a significant advancement over prior art. It eliminates spherical aberration since it is a mathematical property of a parabolic surface to reflect all rays of light incident parallel to the axis into the focal point exactly. The chromatic aberration is avoided since the laws of reflection of light are independent of wavelength. And although the reflection losses on the two parabolic surfaces are similar to the reflection losses on the two mirrors of the prior art's retro reflector, the reflection losses on the lens are completely eliminated.

The benefits of the achromatic functionality of the ORIEs is that a single multipass cell could now be used in infrared, visible or UV spectral regions and that the absence of aberrations and reduced reflection losses permit much higher number of passes thus enabling greatly enhanced sensitivity of the cell.

The light exiting an ORIE can become the entering beam for another ORIE that is confocal with the first ORIE.

Figure 2:
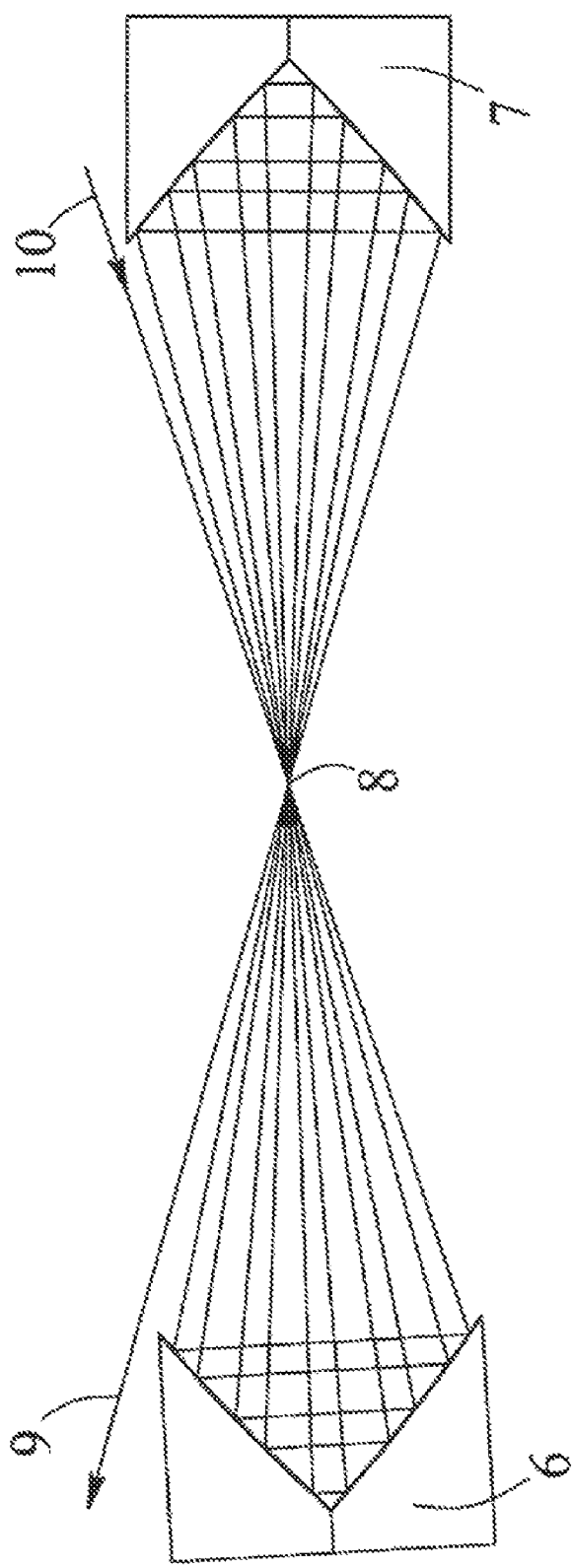
FIG. 2 shows a unipoint multipass transmission configuration achieved by using two opposing ORIEs 6 and 7 arranged around the common focal point 8, where ORIE 6 is slightly rotated around the common focal point 8 to enable the multipass configuration.

FIG. 2 shows a multipass unipoint optical cell made with two ORIEs 6 and 7 arranged around the common focal point 8. The ORIE 6 is slightly rotated around the focal point 8. As a result, the incoming ray 10 is engaged in multiple reflections between the two ORIEs—all passing through the common focal point 8 until, after a number of passes, it escapes out as ray 9. The exact pattern of the reflections and the number of passes through the focal point 8 depend on the exact angle of rotation of the ORIE 6. A different rotation angle produces a different reflection pattern and a different number of passes. Since these ORIEs must accommodate multiple reflections of the beam, they necessarily have to be significantly larger than the cross section of the optical beam used.

Figure 3:
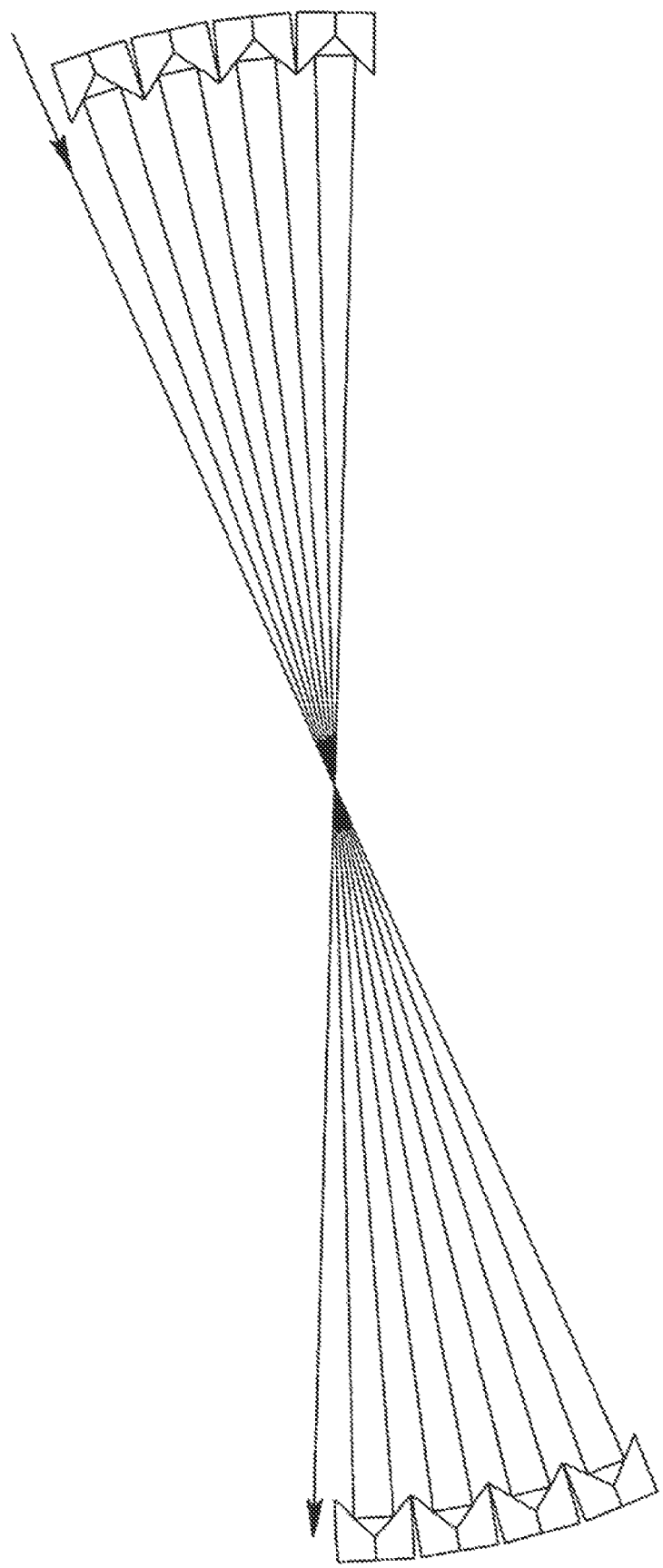
FIG. 3 illustrates how multiple ORIEs can be arranged to enable a unipoint multipass configuration, where each ORIE contributes a single pass.

A different arrangement of the ORIEs that can be used to achieve a unipoint multipass configuration is shown in FIG. 3. Instead of using two large ORIEs, each accommodating multiple passes of the beam, it uses a number of small ORIEs, each just large enough to accommodate a single pass. These ORIEs are positioned around the common focal point. Each ORIE, except for the first, is positioned to receive the beam exiting the previous ORIE and refocus it back into the center and so on for multiple passes. Each ORIE provides a single pass through the common focal point. The multipass unipoint optical cells shown in FIGS. 2 and 3 represent a considerable improvement over the prior art multipass unipoint cell since the number of optical elements is reduced in half. This simplifies the cell construction and alignment and significantly reduces the reflection losses.

Figure 4:
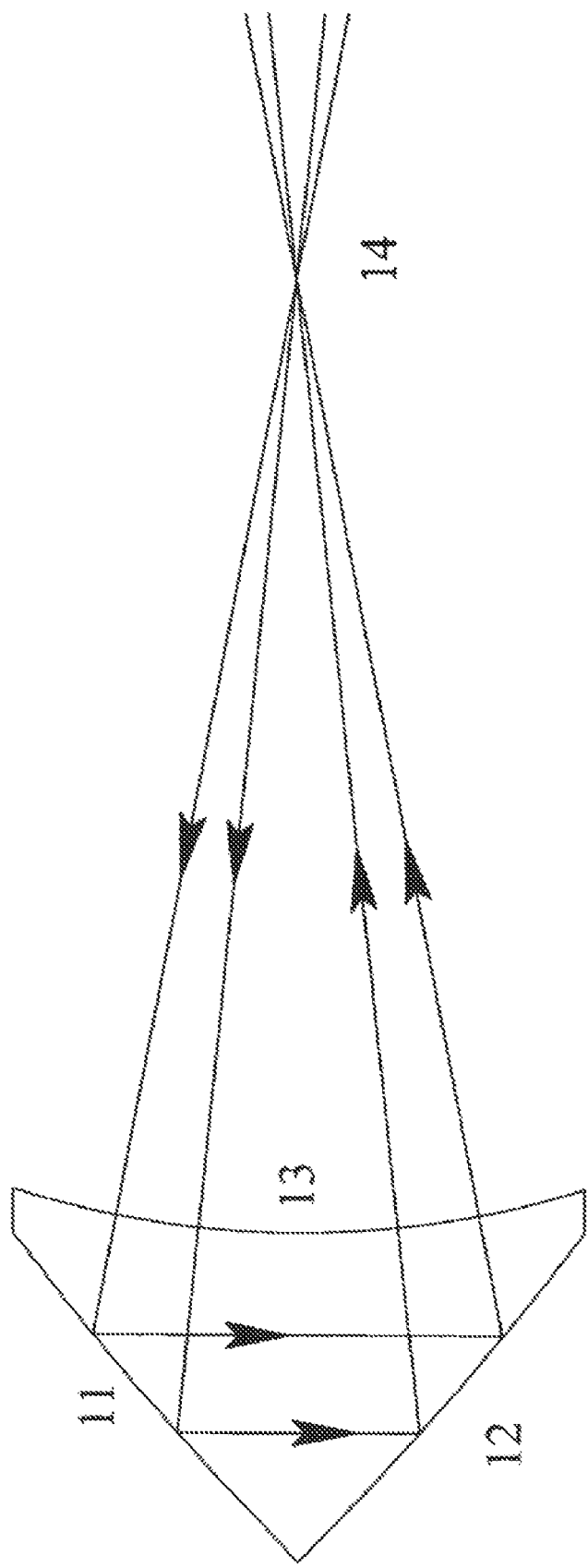
FIG. 4 shows how the ORIE of the present invention can be made out of an optically transparent material; the reflections occurring on the parabolic surfaces 11 and 12 are total internal reflections, while the front surface 13 has a spherical shape with the center of curvature at the common focal point 14, in this way light reflected by the front surface 13 is not lost to the measurement, but is reimaged back to the focal point 14, this is of a particular importance when the multipass unipoint configuration is used to excite Raman scattering or other types of secondary radiation.

If the multipass unipoint optical cell configurations of the present invention are used for the excitation of Raman, fluorescence, etc. by an excitation beam undergoing the multiple passes; it is possible to make the ORIE in such a way to eliminate the negative effects of reflection losses for a broad wavelength range and for both polarizations of excitation light. Such an ORIE is shown in FIG. 4. The internally reflecting parabolic surfaces 11 and 12 are cut into a piece of transparent material. In this way the reflections occurring at the parabolic surfaces 11 and 12 are not regular mirror reflections, which are never lossless, but total internal reflections, which are lossless for any wavelength and polarization of incident light. Point 14 is the common focal point of the two parabolic surfaces. The rays of light coming from the focal point to the reflecting surface 11 have to enter into the transparent material through surface 13. Instead of incurring reflection losses on the parabolic surfaces 11 and 12, this approach leads to reflection losses at the front surface 13 of the solid ORIE. Surface 13 is cut in a spherical shape with the center of curvature coincident with the common focal point 14 of the two parabolic surfaces ensuring that light coming from the focal point 14 impinges perpendicular onto the front surface 13. At surface 13 light is split into two components, one transmitted into the solid ORIE and one reflected and refocused back by the action of the spherical surface 13 into the focal point 14. The transmitted component proceeds through the solid ORIE and is refocused back to focal point 14 by the action of the parabolic surfaces 11 and 12. In transmitting through surface 13 on its way out of the solid ORIE light again impinges perpendicular to surface 13. Thus both reflected and transmitted light return back to the focal point 14 and no light energy is lost in the solid ORIE. If, for instance, laser light is used to excite secondary emissions by the sample, both transmitted and reflected components of the laser light will contribute to the excitement of these secondary emissions. So the special way in which the solid ORIE is made out of a transparent material has for a consequence that the solid ORIE recycles the reflection losses of laser light passing through the element back into the measurement regardless of the wavelength or the polarization of the laser light and in effect eliminates reflection losses.

FIG. 3 shows a unipoint multipass arrangement all contained in one plane. It is however possible to arrange optical reimaging elements around the common focal point in more elaborate ways. In assembling such an arrangement by adding the next ORIE, one is free to rotate the ORIE around the central ray connecting the common focal point and the entrance side of the ORIE. That brings the exit side of the ORIE out of the plane. Each additional ORIE is similarly free to rotate around the central ray coming from the common focal point into the entrance side of said element, so the final configuration can be quite complicated.

Figure 5:
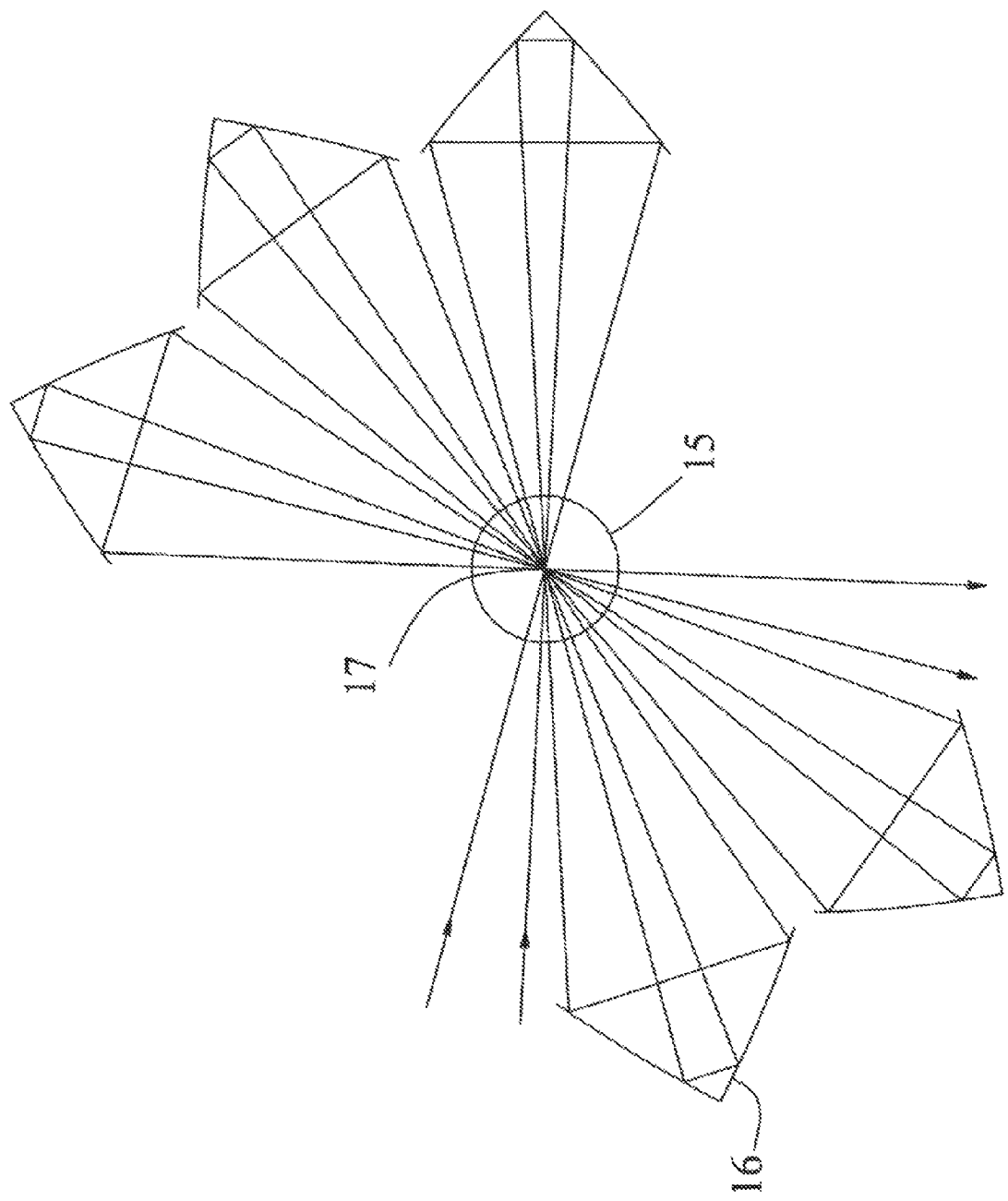
FIG. 5 shows a unipoint multipass configuration that can be used to enhance the sensitivity of both reflectance and ATR spectroscopy, the reflecting element 15 placed in a common focal point is either a reflecting sample or a hemispherical ATR element, several reimaging elements 16 are arranged around the hemisphere with their focal points 17 coincident with the center of curvature of the hemisphere, where all the reimaging elements are arranged in a conical configuration around the hemisphere 15 and the common focus 17 is the apex of the cone.

An assembly consisting of ORIEs arranged in a conical configuration around the common focal point, shown in FIG. 5, can be used for unipoint multipass reflection spectroscopy. The ORIEs can be either solid ORIEs constructed in the manner shown in FIG. 4 or pairs of two individual parabolic mirrors arranged in the manner shown in FIG. 1. A reflecting element is placed in the common focal point at the apex of the cone perpendicular to the cone's axis. This reflecting element can be either a reflecting sample, or a hemispherical ATR element.

If the reflecting sample at the apex of the cone is a metal mirror coated with a very thin film of absorbing material, the film would absorb a miniscule amount of light so that, with a single reflection, it would be very difficult to measure the amount of light absorbed. However, if the above described multipass unipoint cell is used to reflect light multiple times from the surface of the sample, the weak absorbing effect of the thin film is magnified as a function of the number of reflections. By greatly magnifying the effect of thin film absorption, very thin films can now be analyzed by non-contact means. And since all the reflections occur at the same point, the analysis spot can be very small.

Figure 6:
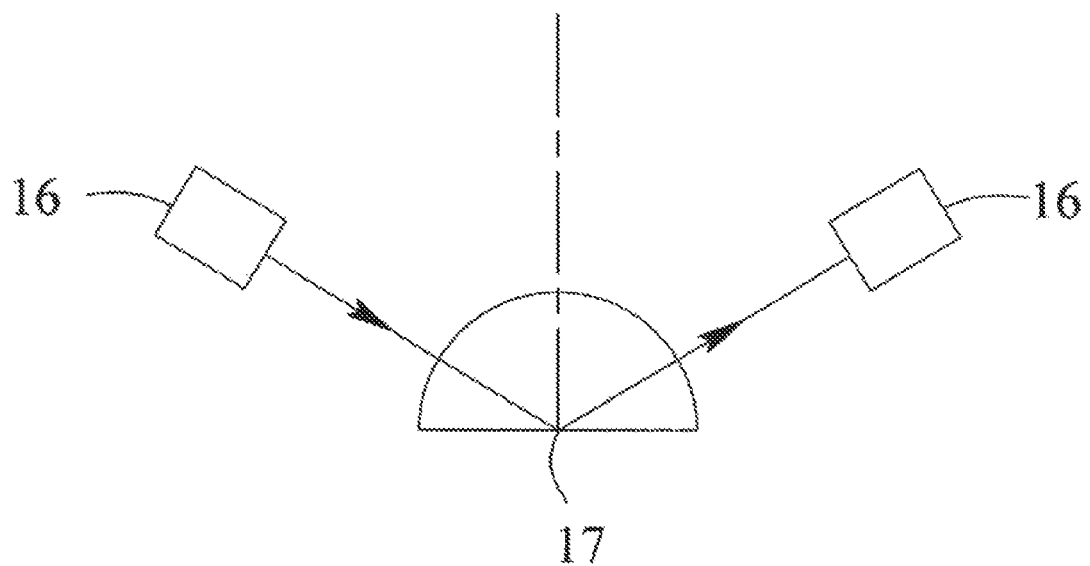
FIG. 6 shows the side view of the ATR element 15, where light is incident into the center 17 of the hemispherical ATR element from a curved side of the hemisphere at an angle of incidence appropriate for internal reflection, after reflection from the flat face of the hemisphere, light exits said hemisphere and is, by an ORIE, refocused again back to the center 17, this is repeated several times by the other ORIEs to magnify the effect of a single reflection, the exiting light may be subsequently spectrally analyzed.

A unipoint multipass configuration that employs a hemispherical ATR element is shown in FIGS. 5 and 6. The optical beam is focused into the center 17 of a hemispherical ATR element 15 at an angle of incidence appropriate for ATR spectroscopy. The angle of incidence is defined as the angle between the normal to the reflecting surface and the incident light. A number of optical reimaging elements 16 are arranged around the hemisphere in a conical arrangement. The axis of the cone is perpendicular to, and centered on the base of the hemisphere. The sample is pressed into contact with the flat face of the hemisphere so that light internally reflects at the sample-hemisphere interface. If the sample absorbs light, the intensity of the reflected light will be attenuated. The reflected light is captured by one of the optical reimaging elements 16 and refocused back to the center of the hemisphere, where it internally reflects, is recaptured and refocused by another element 16, and so on for a number of times. The effect of one reflection is multiplied while always probing the same spot in the center of the hemisphere which is also the common focal point of all the optical reimaging elements 16. This is a significant improvement over the multiple reflection ATR element of the prior art wherein every reflection probes another part of a sample. A small amount of sample placed in contact with the ATR hemisphere can now be analyzed with sensitivity increased in proportion to the number of reflections.

Figure 7:
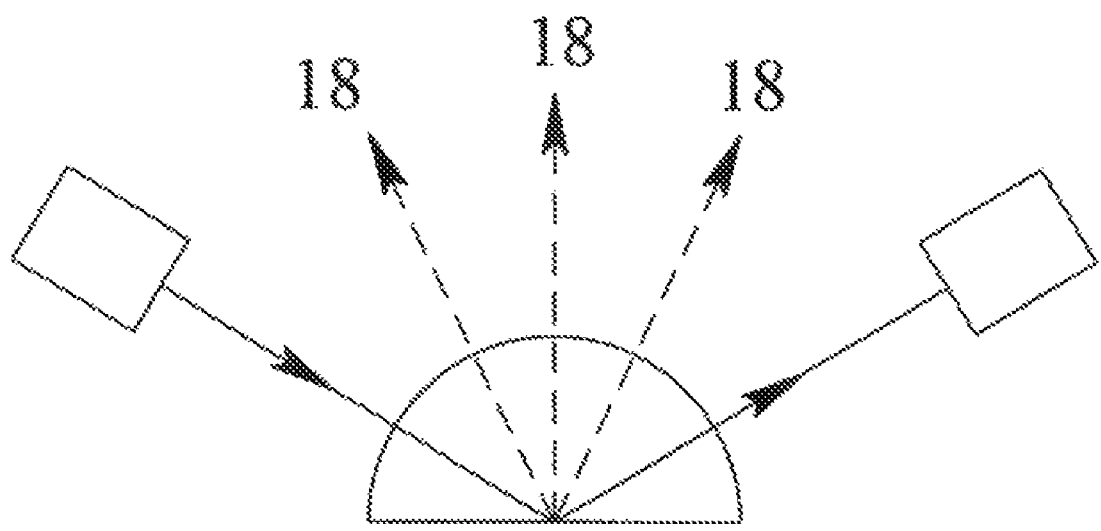
FIG. 7 shows a unipoint multipass configuration that can be used to enhance Raman or other secondary radiation emitted by a sample placed in the center of the hemisphere, this secondary radiation is excited by the excitation light undergoing multiple total internal reflections, the excitation light is brought into the center of a hemispherical optical element for internal reflection, reflected light is captured and refocused back to the center of the hemisphere by the ORIEs arranged in a conical configuration around the hemisphere, secondary radiation 18 excited by the multiple internally reflected light is collected and spectrally analyzed.

A similar assembly of ORIEs arranged in a conical configuration around the common focal point can be used for Raman or fluorescent spectroscopy. The side view of the arrangement is shown in FIG. 7. Laser light is focused into the center of the ATR hemisphere, where it internally reflects, and is returned a large number of times back to the same point for multiple reflections. Raman or fluorescent radiation 18 from the sample excited by the multiple internally reflecting laser beam, and emitted into the solid angle above the hemisphere, is collected and analyzed by a spectrometer. Again, the weak effect of a single reflection is enhanced by the multiple passes.

The present invention is a multipass unipoint optical cell used for the improved analysis of samples by transmission, reflection, Raman or fluorescence spectroscopy by the multiple re-imaging of light through the same analysis point. A number of arrangements for multipass unipoint cells are disclosed. These arrangements are based on a novel ORIE. The ORIE represents a significant advance with respect to prior art. The optical functionality provided by prior art was not exact, only approximate. The same functionality is now provided by ORIE exactly, i.e. without spherical or chromatic aberrations.

The multipass unipoint cells disclosed herein comprise two or more identical ORIEs. An ORIE incorporates a pair of symmetrically opposing confocal coaxial parabolic reflective surfaces that reimage the light exiting the point of analysis back into the same point of analysis at an angle with respect to the incident light. Another ORIE can be placed to accept the light exiting said analysis point and reimage it back to said point, and so on multiple times, each pass at an angle to the previous.

The configuration of the cell can be either for transmission, in which case light passes through the analysis point without changing the direction of travel, or it could be for reflection, in which case light reflects from the sample in the analysis point. At each pass light is either slightly absorbed by the sample, or it excites the sample to emit radiation such as fluorescence or Raman radiation. Since light is brought into repeated interaction with the sample in the analysis point, the effect of the interaction of said light with the same point on said sample is enhanced in proportion to the number of passes. Either light exiting the cell after multiple passes, or the secondary radiation such as Raman or fluorescence emitted by the sample in response to the light passing through the cell multiple times, are analyzed by a spectrometer providing detailed analytical information about the sample.

While the above description contains many specificities, these should not be construed as limitations on the scope of the invention, but rather as an exemplifications of several preferred embodiments thereof. Many other variations are possible. For example, the larger mirror pair elements accommodating multiple passes could be combined into the multi-element arrangement shown in FIG. 5. Accordingly, the scope of the invention should be determined not by the embodiments illustrated, but by the appended claims and their legal equivalents.

The disclosed invention has many advantages. The first advantage is that this invention advances prior art by disclosing the ORIE that performs the desired optical function exactly, not approximately as done by the prior art that suffered from both the spherical and the chromatic aberrations. The second advantage is that herein disclosed ORIE utilizes fewer optical surfaces to achieve said functionality with fewer losses than prior art. These advantages made feasible the various configurations of multipass unipoint cells described herein. The multipass unipoint cells advance the art of spectroscopic sample analysis by extending said analysis to the reflection and ATR modes of spectroscopy. A unique ORIE made out of a transparent optical material enables a multipass unipoint cell for the excitation of Raman and fluorescent radiation that, by virtue of its shape, completely eliminates reflection losses in the entire spectral range within which said optical material is transparent. Prior art could only minimize said reflection losses in a narrow spectral range and only for one of the two polarizations of incident light.

It should be noted that the terms "first", "second", and "third", and the like may be used herein to modify elements performing similar and/or analogous functions. These modifiers do not imply a spatial, sequential, or hierarchical order to the modified elements unless specifically stated.

While the disclosure has been described with reference to several embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiments disclosed as the best mode contemplated for carrying out this disclosure, but that the disclosure will include all embodiments falling within the scope of the appended claims.

What is claimed is:

1. An optical reimaging element comprising:
   a first off-axis parabolic mirror having only the portion of the mirror surface below the first plane that passes through its focal point and is perpendicular to the axis of the first parabola associated with said first mirror, said portion of said first mirror being on the same side of said first plane as the vertex of said first parabola;
   a second off axis parabolic mirror identical to the first mirror also having only the portion of the mirror surface below the second plane that passes through its focal point and is perpendicular to the axis of the second parabola associated with said second mirror, said portion of said second mirror being on the same side of said second plane as the vertex of said second parabola; and
   said first and second mirrors being in optical communication with each other so that their said first and second planes coincide and so that their parabolic mirror surfaces are symmetrically opposing, confocal, and coaxial thereby having the property that a ray of light coming from the common focal point of said parabolic mirrors and incident onto one of said parabolic mirrors reflects to other said parabolic mirror wherein it reflects back to said focal point, but at an angle with the direction in which it left said focal point.

2. A cell comprising two optical reimaging elements from claim 1 arranged on opposite sides of said common focal point with one of said elements slightly rotated around said focal point to provide a multipass configuration, enabling the analysis of a sample placed in said focal point by transmission, Raman, or fluorescence spectroscopy.

3. A cell comprising multiple optical reimaging elements from claim 1 arranged around said common focal point in such a way that light reimaged into said focal point by one of said elements enters another creating in such a way a multipass configuration to enable the analysis of a sample placed in said focal point by transmission, Raman or fluorescence spectroscopy.

4. A cell comprising two optical reimaging elements from claim 1 where a multipass arrangement is assembled to enable multiple reflections from a reflecting sample placed in said common focal point wherein said optical elements are inclined symmetrically with respect to said reflecting sample so that light coming to said focal point from one said optical element is reflected from said reflecting sample into another said element to enable the analysis of said reflecting sample, placed in said focal point, by reflection, Raman, or fluorescence spectroscopy.

5. A cell comprising a number of optical reimaging elements from claim 1 wherein a multipass arrangement is assembled to enable multiple reflections from a reflecting sample placed in said common focal point and wherein said optical elements are arranged in a conical configuration with said common focal point at the vertex of the cone to enable the analysis of said sample, placed in said focal point, by reflection, Raman, or fluorescence spectroscopy.

6. The optical reimaging element of claim 1, where there is no lens in the light pathway between the focal point and the first and second parabolic mirrors.

7. An optical reimaging element comprising:
   a material, said material comprising:
      a top face;
      a bottom face;
      a first side face;
      a second side face;
      a third side face; and
   wherein the first and second of the side faces are in the shape of two symmetrically opposing, confocal, and coaxial parabolic surfaces so that the common axis of said parabolic surfaces is parallel and midway between said top and bottom faces and the third side face is spherical with the center of curvature coincident with said common focal point of said parabolic surfaces so that any ray of light originating from said common focal point and directed to said element is incident normal to said third face, transmits into said element without changing direction, is incident on one of said parabolic surfaces, reflects by total internal reflection to the other of said two parabolic surfaces, is reflected again by total internal reflection to come at normal incidence to said third face, transmits out of said element without changing direction and returns to said common focal point at an angle to the direction in which it left said focal point.

8. A cell comprising two optical reimaging elements from claim 7 arranged on opposite sides of said common focal point with one of said elements slightly rotated around said focal point to provide a multipass configuration, enabling the analysis of a sample placed in said focal point by transmission, Raman or fluorescence spectroscopy wherein the reflections on the front surfaces of said elements are recycled back into the measurement while the reflections on said two parabolic surfaces are total internal reflections and therefore lossless.

9. A cell comprising a number of optical reimaging elements from claim 7 arranged around said common focal point in such a way that light reimaged into said focal point by one of said elements enters another creating in such a way a multipass configuration to enable the analysis of a sample placed in said focal point by transmission, Raman or fluorescence spectroscopy wherein the reflections on said front surfaces of said elements are recycled back into the measurement while the reflections on the said parabolic surfaces are total internal reflections and therefore lossless.

10. A cell comprising two optical reimaging elements from claim 7 where a multipass arrangement is assembled to enable multiple reflections from a reflecting sample placed in said common focal point and wherein said optical elements are inclined symmetrically with respect to said reflecting sample so that light coming to said focal point from one said optical element is reflected from said reflecting sample into another said element to enable the analysis of said reflecting sample, placed in said focal point, by reflection, Raman, or fluorescence spectroscopy.

11. The cell from claim 10 with a hemispherical attenuated total reflection element placed centered into said common focal point with its flat face replacing said reflecting sample so that reflections in said focal point are internal reflections, enabling the analysis of samples, brought in contact with the flat surface of said hemispherical element in said focal point, by internal reflection, Raman, or fluorescence spectroscopy.

12. A cell comprising a number of optical reimaging elements from claim 7 wherein a multipass arrangement is assembled to enable multiple reflections from a reflecting sample placed in said common focal point and wherein said optical elements are arranged in a conical configuration with said common focal point at the vertex of the cone to enable the analysis of said sample, placed in said focal point, by reflection, Raman, or fluorescence spectroscopy.

13. The cell from claim 12 with a hemispherical attenuated total reflection element placed centered on said vertex of and coaxial with said cone so that reflections in said focal point are internal reflections, enabling the analysis of a sample, brought in contact with the flat surface of said hemispherical element in said focal point, by internal reflection, Raman, or fluorescence spectroscopy.

14. The optical reimaging element of claim 7, where there is no lens in the light pathway between the focal point and the first and second side faces.

* * * * *